(12) United States Patent
Paxman et al.

(10) Patent No.: US 11,039,952 B2
(45) Date of Patent: Jun. 22, 2021

(54) TEMPERATURE CONTROL SYSTEM

(71) Applicant: Paxman Coolers Limited, Huddersfield (GB)

(72) Inventors: Glenn Alan Paxman, Holmfirth (GB); Neil Eric Paxman, Holmfirth (GB)

(73) Assignee: PAXMAN COOLERS LIMITED, Huddersfield (GB)

( * ) Notice: Subject to any disclaimer, the term of this patent is extended or adjusted under 35 U.S.C. 154(b) by 778 days.

(21) Appl. No.: 15/512,785

(22) PCT Filed: Sep. 22, 2015

(86) PCT No.: PCT/GB2015/052741
§ 371 (c)(1),
(2) Date: Mar. 20, 2017

(87) PCT Pub. No.: WO2016/046536
PCT Pub. Date: Mar. 31, 2016

(65) Prior Publication Data
US 2017/0296379 A1    Oct. 19, 2017

(30) Foreign Application Priority Data

Sep. 23, 2014 (GB) .................................... 1416761

(51) Int. Cl.
*A61F 7/00* (2006.01)
*A61F 7/02* (2006.01)
(Continued)

(52) U.S. Cl.
CPC .............. *A61F 7/0085* (2013.01); *A01G 7/00* (2013.01); *A61F 7/02* (2013.01); *F25B 49/02* (2013.01);
(Continued)

(58) Field of Classification Search
CPC combination set(s) only.
See application file for complete search history.

(56) References Cited

U.S. PATENT DOCUMENTS 1,404,320 A    1/1922   Roberts et al.
1,896,953 A    2/1933   Hassell
(Continued)

FOREIGN PATENT DOCUMENTS

CN    2406636 Y    11/2000
DE    1454922 A1    4/1969
(Continued)

*Primary Examiner* — Joseph A Stoklosa
*Assistant Examiner* — Adam J Avigan
(74) *Attorney, Agent, or Firm* — Coats & Bennett, PLLC

(57) ABSTRACT

A temperature control system comprising a first peripheral fluid circuit for the passage of a first heat exchanger fluid. The first peripheral fluid circuit comprises a first fluid connection for fluidly connecting a first peripheral heat exchanger in series with a first peripheral-evaporator heat exchanger. There is also provided a first peripheral pump for pumping the first heat exchanger fluid around the first peripheral fluid circuit. There is also provided a first evaporator circuit for the passage of an evaporator heat exchanger fluid through the first peripheral-evaporator heat exchanger. The first evaporator circuit comprises a first evaporator pump for pumping the evaporator heat exchanger fluid around the first evaporator circuit. The first evaporator circuit is fluidly isolated from the first peripheral fluid circuit. The first peripheral-evaporator heat exchanger is configured to permit heat exchange between the heat exchanger fluids.

17 Claims, 3 Drawing Sheets

(51) Int. Cl.
*A01G 7/00* (2006.01)
*F25B 49/02* (2006.01)
*G05B 15/02* (2006.01)

(52) U.S. Cl.
CPC ...... *G05B 15/02* (2013.01); *A61F 2007/0056* (2013.01); *A61F 2007/0093* (2013.01); *A61F 2007/0096* (2013.01); *A61F 2007/0233* (2013.01); *A61F 2007/0295* (2013.01)

(56) References Cited

U.S. PATENT DOCUMENTS

| | | | |
|---|---|---|---|
| 2,726,658 | A | 12/1955 | Chessey |
| 3,242,245 | A | 3/1966 | Greig et al. |
| 3,256,565 | A | 6/1966 | Alesi et al. |
| 3,867,939 | A | 2/1975 | Moore et al. |
| 4,566,455 | A | 1/1986 | Kramer |
| 4,987,896 | A | 1/1991 | Nakamatsu |
| 5,086,771 | A | 2/1992 | Molloy |
| 5,169,384 | A | 12/1992 | Bosniak et al. |
| 5,342,411 | A | 8/1994 | Maxted et al. |
| 5,469,579 | A | 11/1995 | Tremblay et al. |
| 5,603,728 | A | 2/1997 | Pachys |
| 5,630,230 | A | 5/1997 | Fujino et al. |
| 5,802,865 | A | 9/1998 | Strauss |
| 5,895,418 | A | 4/1999 | Saringer |
| 5,950,234 | A | 9/1999 | Leong et al. |
| 6,117,164 | A | 9/2000 | Gildersleeve et al. |
| 6,156,059 | A | 12/2000 | Olofsson |
| 6,178,562 | B1 | 1/2001 | Elkins |
| 6,312,453 | B1 | 11/2001 | Stefanile et al. |
| 6,375,674 | B1 | 4/2002 | Carson |
| 6,427,467 | B1 | 8/2002 | Bell |
| 6,681,590 | B1 | 1/2004 | Jones |
| 7,721,349 | B1 | 5/2010 | Strauss |
| 2002/0058976 | A1 | 5/2002 | Lee |
| 2002/0091431 | A1 | 7/2002 | Gunn et al. |
| 2003/0088299 | A1* | 5/2003 | Magers ............... A61F 7/12 607/104 |
| 2005/0028551 | A1* | 2/2005 | Noda ............... F04C 29/0064 62/434 |
| 2005/0107855 | A1 | 5/2005 | Lennox et al. |
| 2005/0132468 | A1 | 6/2005 | Lundgren |
| 2005/0187502 | A1 | 8/2005 | Krempel et al. |
| 2006/0235496 | A1 | 10/2006 | Collins et al. |
| 2008/0184456 | A1 | 8/2008 | Fontanez |
| 2008/0228248 | A1 | 9/2008 | Guyuron et al. |
| 2008/0269852 | A1 | 10/2008 | Lennox et al. |
| 2009/0054958 | A1 | 2/2009 | Nofzinger |
| 2010/0030306 | A1 | 2/2010 | Edelman et al. |
| 2010/0095641 | A1 | 4/2010 | Ruetenik |
| 2010/0186436 | A1 | 7/2010 | Stormby |
| 2010/0319110 | A1 | 12/2010 | Preston-Powers |
| 2011/0137249 | A1* | 6/2011 | Collins ............... A61F 7/12 604/113 |
| 2012/0283534 | A1 | 11/2012 | Carr et al. |
| 2013/0138185 | A1 | 5/2013 | Paxman et al. |
| 2013/0226044 | A1 | 8/2013 | Moore et al. |
| 2013/0276469 | A1 | 10/2013 | Dryzun |
| 2014/0046410 | A1 | 2/2014 | Wyatt |
| 2014/0172050 | A1 | 6/2014 | Dabrowiak |
| 2014/0222121 | A1 | 8/2014 | Spence et al. |
| 2014/0276253 | A1 | 9/2014 | Varga et al. |
| 2014/0277302 | A1 | 9/2014 | Weber et al. |

FOREIGN PATENT DOCUMENTS

| | | |
|---|---|---|
| DE | 102011100616 A1 | 11/2011 |
| EP | 1520568 A1 | 4/2005 |
| GB | 2323915 A | 10/1998 |
| GB | 2482792 A | 2/2012 |
| JP | 05278081 A | 10/1993 |
| JP | 2002316357 A | 10/2002 |
| KR | 20070088224 A | 8/2007 |
| WO | 0003666 A1 | 1/2000 |
| WO | 0038601 A1 | 7/2000 |
| WO | 0162193 A2 | 8/2001 |
| WO | 0200132 A1 | 1/2002 |
| WO | 2006110405 A2 | 10/2006 |
| WO | 2013074128 A2 | 5/2013 |
| WO | 2013190333 A2 | 12/2013 |

\* cited by examiner

TEMPERATURE CONTROL SYSTEM

BACKGROUND

Various medical treatments involve temperature control of a body part. In the treatment of cancer, it is known to cool the head of a patient during chemotherapy in order to reduce the extent and/or likelihood of hair loss.

FIG. 1 shows a schematic overview of a temperature control system 10 of related art document GB2482792B which defines a prior solution of the applicant.

There is shown an example of a known cooling cap 210. The cooling cap 210 comprises a single tube 211 in a concentric hoop arrangement, stacked on top of itself, to form a part spherical garment to be worn on a patient's head. The tube 211 has a fluid inlet 212 and a fluid outlet 214. In use, coolant is pumped around the cap, from the inlet 212 to the outlet 214, via a temperature control system 10 which regulates the temperature of the coolant to thereby remove heat from a contact area with the patient.

The temperature control system 10 is provided with two such caps 210,210a. Lengths of flexible hosing 220 connect each cap 210 to a refrigeration and control unit 100 of the temperature control system 10.

The refrigeration and control unit 100 comprises a heat exchanger 110, a pump 120 and a controller 130 arranged to output control signals via outputs 131 and 132 to control operation of the heat exchanger 110 and pump 120, respectively.

The controller 130 is also connected to a computer memory 138 and the user interface 139.

Although the system provides effective cooling, the system may not respond to a demand for a high heat transfer rate to/from the fluid in the heat exchanger 110, the heat transfer process being a function of the fluid flow rate and the cooling capacity of the heat exchanger 110. Also, cooling requirements of a patient wearing one of the caps might not match those of another patient wearing the other cap. This may lead to patient discomfort through over cooling, or ineffective treatment due to insufficient cooling, either of which may result in the patient stopping treatment altogether. This may limit the desirability of such a system.

Hence a temperature control system which is more adaptable to individual patient needs is highly desirable.

SUMMARY

According to the present invention there is provided apparatus, system and a method as set forth in the appended claims. Other features of the invention will be apparent from the dependent claims, and the description which follows.

Accordingly there may be provided a temperature control system (300) comprising: a first peripheral fluid circuit (312) for the passage of a first heat exchanger fluid, the first peripheral fluid circuit (312) comprising: a first fluid connection (314) for fluidly connecting a first peripheral heat exchanger (310) in series with a first peripheral-evaporator heat exchanger (316); and a first peripheral pump (318) for pumping the first heat exchanger fluid around the first peripheral fluid circuit (312); a first evaporator circuit (320) for the passage of an evaporator heat exchanger fluid through the first peripheral-evaporator heat exchanger (316), the first evaporator circuit (320) comprising: a first evaporator pump (322) for pumping the evaporator heat exchanger fluid around the first evaporator circuit (320); the first evaporator circuit (320) being fluidly isolated from the first peripheral fluid circuit (312); and the first peripheral-evaporator heat exchanger (316) being configured to permit heat exchange between the heat exchanger fluids.

A first heat exchanger fluid reservoir (324) may be provided in the first peripheral fluid circuit (312) in series with the first peripheral-evaporator heat exchanger (316) and first peripheral pump (318).

A first peripheral heat exchanger (310) may be fluidly connected to the first fluid connection (314) such that the first peripheral heat exchanger (310) is in series with the first peripheral-evaporator heat exchanger (316) and first peripheral pump (318).

The first evaporator circuit (320) may comprise an evaporator tank (326) in series with the first peripheral-evaporator heat exchanger (316) and first evaporator pump (322), the first evaporator pump (322) being operable to pump the evaporator heat exchanger fluid from the evaporator tank (326) to the first peripheral-evaporator heat exchanger (316) and back to the evaporator tank (326).

There may also be provided a second peripheral fluid circuit (312') for the passage of a second heat exchanger fluid, the second peripheral circuit (312') comprising: a second fluid connection (314') for fluidly connecting a second peripheral heat exchanger (310') in series with a second peripheral-evaporator heat exchanger (316'); and a second peripheral pump (318') for pumping the second heat exchanger fluid around the second peripheral circuit (312'); a second evaporator circuit (320') for the passage of the evaporator heat exchanger fluid through the further heat exchanger (316'), the second evaporator circuit (320') comprising: a second evaporator pump (322') for pumping the evaporator heat exchanger fluid around the second evaporator circuit (320'); the second evaporator circuit (320') being fluidly isolated from the second peripheral circuit (312') and the second peripheral-evaporator heat exchanger (316') being configured to permit heat exchange between the heat exchanger fluids.

A second heat exchanger fluid reservoir (324') may be provided in the second peripheral circuit (312') in series with the second peripheral-evaporator heat exchanger (316') and second peripheral pump (318').

A second peripheral heat exchanger (310') may be fluidly connected to the second fluid connection (314') such that the second peripheral heat exchanger (310') is in series with the second peripheral-evaporator heat exchanger (316') and second peripheral pump (318').

The second peripheral circuit (312') may be in fluid communication with the evaporator tank (326) such that the second peripheral-evaporator heat exchanger (316') is in series with the evaporator tank (326') and second evaporator pump (322'), the second evaporator pump (322') being operable to pump the evaporator heat exchanger fluid from the evaporator tank (326) to the second peripheral-evaporator heat exchanger (316') and back to the evaporator tank (326).

The or each fluid circuit may be closed. That is to say, each fluid circuit may be a closed circuit.

The first peripheral fluid circuit (312) may be fluidly isolated from the second peripheral fluid circuit (312').

The evaporator tank (326) may be provided with an evaporator (330) the evaporator (330) being in series fluid communication with a compressor (332) and condenser (334) via a refrigerant fluid circuit (336) to thereby provide a flow path for a refrigerant.

There may be provided at least one temperature sensor (340,342;340',342') in the peripheral fluid circuit (312,312') for the measurement of temperature of heat exchanger fluid in said circuit (312,312').

There may be provided an inlet temperature sensor (340, 340') upstream of the peripheral heat exchanger (310,310'), and an outlet temperature sensor (342,342') downstream of the peripheral heat exchanger (310,310').

There may be provided a controller (350) in communication with the pumps (318,322;318',322'), and which controls the pumps in dependence upon signals indicative of temperature received from the temperature sensor(s) (340, 342;340',342').

The peripheral pump (318, 318') and/or evaporator pump (322,322') may be controllable in dependence upon the temperature of their respective peripheral heat exchanger fluids to regulate the fluid flow rate through their respective fluid circuits.

The first peripheral pump (318) and/or evaporator pump (322) may be controllable in dependence upon a measured, determined and/or derived heat exchange rate of the first peripheral heat exchanger (310) to regulate the fluid flow rate through their respective fluid circuits.

At least one of the first peripheral fluid circuit pumps (318,318') and/or evaporator circuit pumps (322,322') may be controllable such that the flow rates through their respective fluid circuits may be substantially equal to one another and may also be different to one another.

The system may be configured to maintain the temperature of the evaporator heat exchanger fluid at a temperature different to the peripheral heat exchanger fluid.

The system may be configured to maintain the temperature of the evaporator heat exchanger fluid at a temperature lower than the peripheral heat exchanger fluid.

The flow of fluid through the circuits may be controllable to provide a heat exchange rate schedule through the peripheral heat exchangers (310,310') as required, desired, pre-set, chosen and/or adjusted by the user.

There is thus provided a temperature control system with a highly adaptable heat transfer performance. The device of the present disclosure is configured to achieve more accurate and responsive heat regulation than devices of the related art.

BRIEF DESCRIPTION OF THE DRAWINGS

Examples of the present disclosure will now be described with reference to the accompanying drawings, in which.

DETAILED DESCRIPTION

Figure 1:
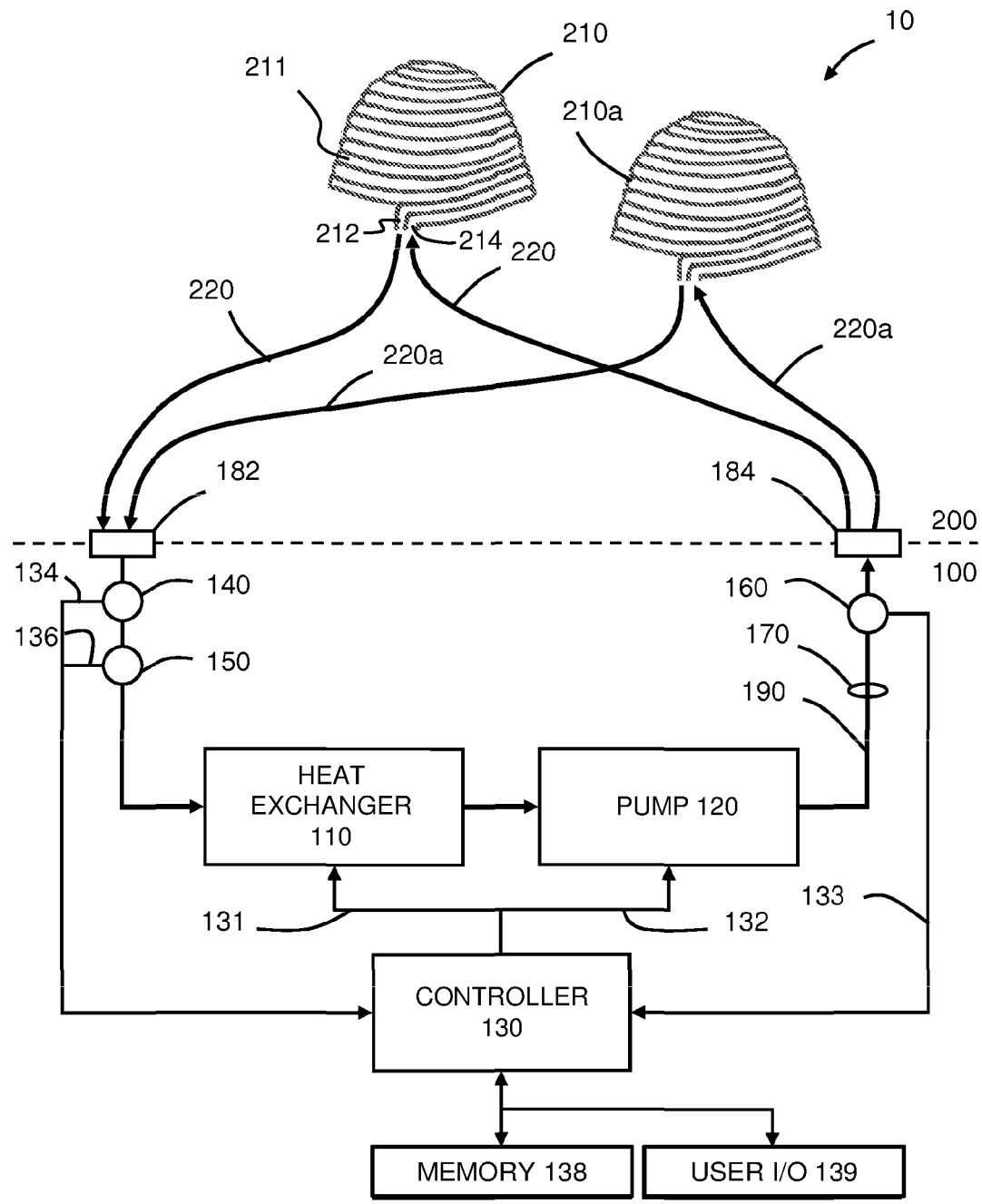
FIG. 1 shows a schematic representation of a temperature regulation system of the related art, discussed previously.
Figure 2:
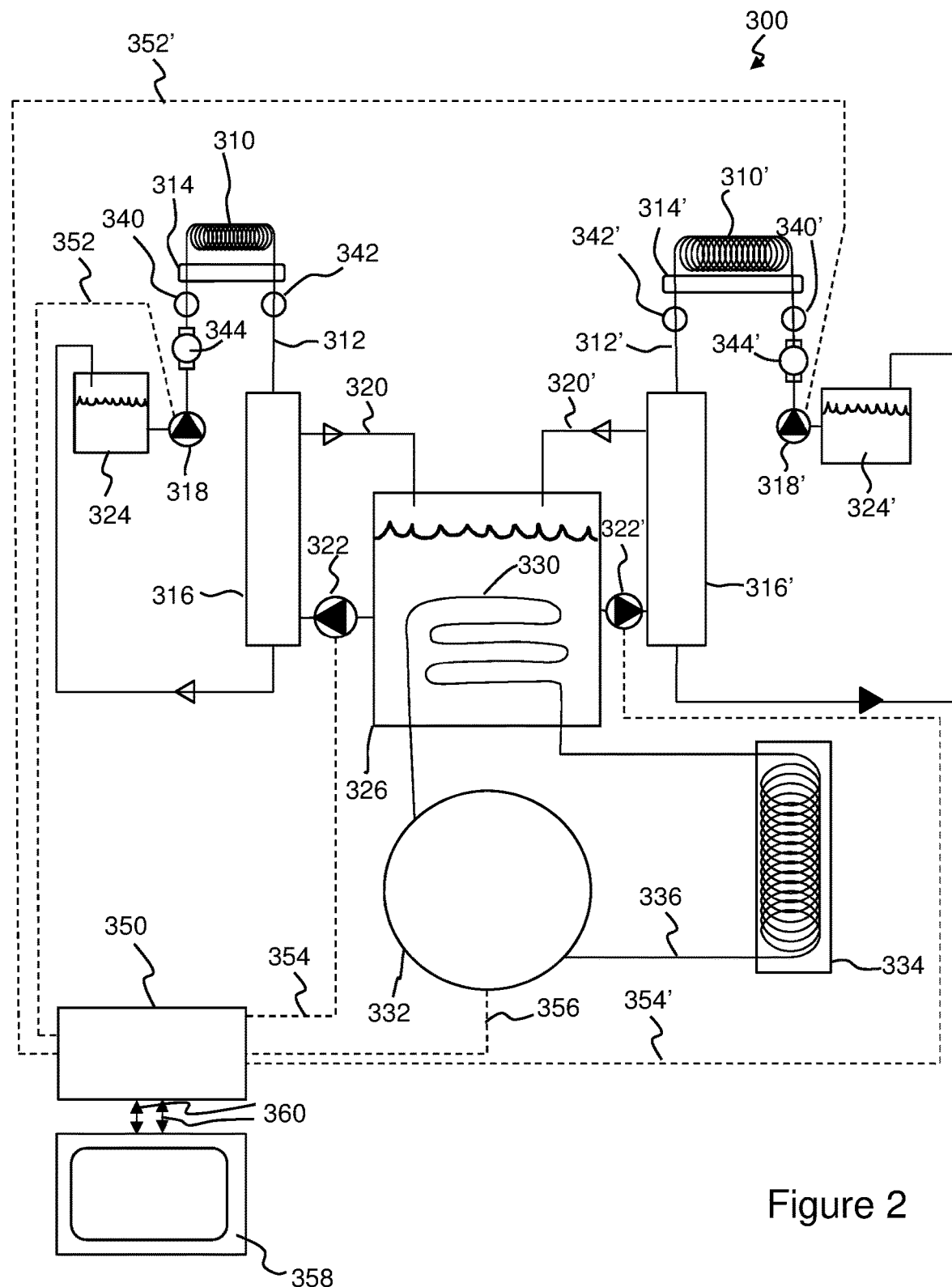
FIG. 2 shows a schematic representation of a temperature control system according to the present disclosure.
Figure 3:
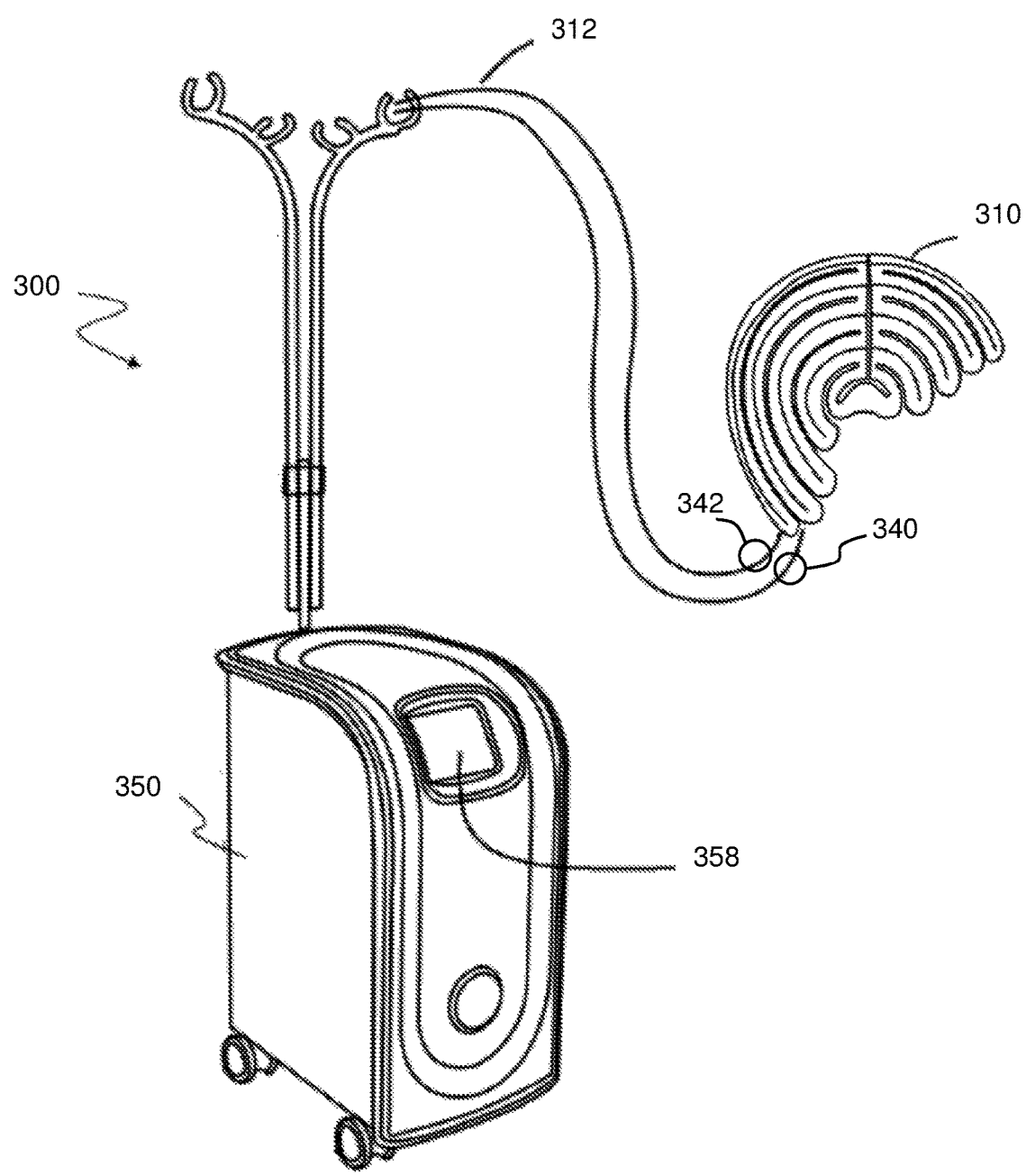
FIG. 3 shows a pictorial representation of the temperature control system according to the present disclosure.

An example of a fluid temperature control system 300 according to the present disclosure is shown represented in FIG. 2. A representation of what it may look like in reality is shown in FIG. 3. There is shown a dual system configured for the supply of temperature regulation fluid to two heat exchangers 310,310' configured to be interfaces between the system 300 and the object to be cooled, warmed or maintained at a constant temperature. FIG. 2 shows two heat exchangers 310,310' attached. In the example of FIG. 3, while two heat exchangers 310,310' may be attached, only one is attached as the system 300 may also be operated with a single heat exchanger 310 attached. The heat exchangers 310,310' may be garments to be worn by a human or animal, for example a cap (to be worn on a head) or a sleeve (to be worn around an arm, leg or torso). The heat exchanger may also be used in conjunction with other applications, for example the temperature regulation of a fluid system by being wrapped around a conduit to keep the fluid flowing through it at a certain temperature, as part of a computer system for removing heat, or for use in plant incubators to maintain plant beds at a desired temperature during germination.

In the example shown in FIG. 2, the temperature control system comprises an evaporator tank 326 and two outer (or "peripheral") fluid circuits (312,312') linked to the evaporator tank 326, to which the heat exchangers 310,310' are attached.

Hence the temperature control system 300 comprises a first peripheral fluid circuit 312 for the passage of a first heat exchanger fluid. The first peripheral fluid circuit 312 comprises a first fluid connection 314 for fluidly connecting the first peripheral heat exchanger 310 (i.e "heat exchanger") in series with a first peripheral-evaporator heat exchanger 316 and a first peripheral pump 318 for pumping the first heat exchanger fluid around the first peripheral fluid circuit 312. In operation the cyclic direction of flow in the peripheral circuit is from the pump 318, through the peripheral heat exchanger 310 to the peripheral-evaporator heat exchanger 316, into the peripheral reservoir 324, and back to the peripheral pump 318.

The term "peripheral-evaporator heat exchanger" is intended to identify the heat exchanger (as shown in the drawings) as the heat exchanger 316,316' which acts as an interface between the peripheral fluid circuit 312, 312' and an evaporator fluid circuit 320 described below.

In FIG. 2 the heat exchanger 310 is fluidly connected to the first fluid connection 314 such that the first peripheral heat exchanger 310 is in series with the first peripheral-evaporator heat exchanger 316 and first peripheral pump 318. However, the heat exchanger 310 may be dis-engageable from, and re-engageable with, the rest of system 300.

A first heat exchanger fluid reservoir 324 is provided in the first peripheral fluid circuit 312 in series with the first peripheral-evaporator heat exchanger 316 and first peripheral pump 318.

The first evaporator circuit 320 is provided for the passage of an evaporator heat exchanger fluid through the first peripheral-evaporator heat exchanger 316. The first evaporator circuit 320 comprises a first evaporator pump 322 for pumping the evaporator heat exchanger fluid around the first evaporator circuit 320. The first evaporator circuit 320 also comprises an evaporator tank 326 in series with the first peripheral-evaporator heat exchanger 316 and first evaporator pump 322. The first evaporator pump 322 is operable to pump the evaporator heat exchanger fluid from the evaporator tank 326 to the first peripheral-evaporator heat exchanger 316 and back to the evaporator tank 326.

In operation the direction of flow in the evaporator circuit is from the evaporator pump 322, through the peripheral-evaporator heat exchanger 316, into the peripheral reservoir evaporator tank 326, and back to the evaporator pump 322.

The first evaporator circuit 320 is fluidly isolated from the first peripheral fluid circuit 312. The first peripheral-evaporator heat exchanger 316 is configured to permit heat exchange between the heat exchanger fluids.

The temperature control system 300 further comprises a second peripheral fluid circuit 312' for the passage of a second heat exchanger fluid. The second peripheral fluid circuit 312' is essentially identical to the first peripheral fluid circuit 312, and hence like features are indicated with the same reference numeral as that described with reference to the first fluid circuit 312, except the reference number is followed by a "'". The second peripheral circuit 312' comprises a second fluid connection 314' for fluidly connecting a second peripheral heat exchanger 310' in series with a second peripheral-evaporator heat exchanger 316', and a second peripheral pump 318' for pumping the second heat exchanger fluid around the second peripheral circuit 312'.

In the example shown, a second peripheral heat exchanger 310' is fluidly connected to the second fluid connection 314' such that the second peripheral heat exchanger 310' is in series with the second peripheral-evaporator heat exchanger 316' and second peripheral pump 318'. However, the heat exchanger 310' may be dis-engageable from, and re-engageable with, the rest of system 300.

A second heat exchanger fluid reservoir 324' is provided in the second peripheral circuit 312' in series with the second peripheral-evaporator heat exchanger 316' and second peripheral pump 318'.

The temperature control system 300 further comprises a second evaporator circuit 320' for the passage of the evaporator heat exchanger fluid through the further heat exchanger 316', the second evaporator circuit 320' comprising a second evaporator pump 322' for pumping the evaporator heat exchanger fluid around the second evaporator circuit 320'. The second evaporator circuit 320' is fluidly isolated from the second peripheral circuit 312' and the second peripheral-evaporator heat exchanger 316' is configured to permit heat exchange between the heat exchanger fluids.

The second evaporator circuit 320' is in fluid communication with the evaporator tank 326 such that the second peripheral-evaporator heat exchanger 316' is in series with the evaporator tank 326' and second evaporator pump 322'. The second evaporator pump 322' is operable to pump the evaporator heat exchanger fluid from the evaporator tank 326 to the second peripheral-evaporator heat exchanger 316' and back to the evaporator tank 326.

Each fluid circuit is a closed circuit. The first peripheral fluid circuit (312) is fluidly isolated from the second peripheral fluid circuit (312')

Although two peripheral fluid circuits 312,312' and evaporator circuits 320, 320' are shown for two heat exchangers 310,310', there may be provided only one peripheral fluid circuit 310 and evaporator circuit 320. In an alternative example, there may be provided three or more peripheral fluid circuits and evaporator circuits for three or more heat object interface heat exchangers.

The evaporator tank 326 is provided with an evaporator 330, the evaporator 330 being in series fluid communication with a compressor 332 and condenser 334 via a refrigerant fluid circuit 336 to thereby provide a flow path for a refrigerant.

There is provided at least one temperature sensor 340, 342;340',342' in the peripheral fluid circuit 312,312' for the measurement of temperature of heat exchanger fluid in said circuit 312,312'. As shown in the example in FIG. 2, there is provided an inlet temperature sensor 340,340' upstream of the peripheral heat exchanger (310,310'), and an outlet temperature sensor downstream of the peripheral heat exchanger 310,310'. That is to say, the system 300 further comprises inlet temperature sensors 340,340' located in a region of the fluid circuit 312,312' which delivers heat exchanger fluid to the heat exchanger 310, 310' and an outlet temperature sensor 342,342' located in a region of the fluid circuit 312,312' which receives heat exchanger fluid from the heat exchanger 310,310'.

There is also provided at least one fluid flow sensor 344;344' in the peripheral fluid circuit 312,312', for the determination of mass flow of fluid through the peripheral fluid circuit 312,312'.

The system further comprises a controller 350 in communication with the pumps 318,322;318',322', and which controls the pumps in dependence upon signals indicative of temperature received from the temperature sensor(s) 340, 342;340',342' and fluid flow sensor 344;344'. That is to say, the temperature sensors 340,342;340'342' and fluid flow sensor 344;344' communicate data to a controller 350 (for example wirelessly or via communication lines (not shown)). The controller 350 also is in communication with each of the pumps 318,322;318',322' via communication lines 352,354;352',354' respectively. Likewise the controller 350 is in communication with the evaporator compressor 332 via a communication line 356.

In turn, the controller 350 is linked to a user interface 358 via communication lines 360. The user interface 358 and/or controller 350 may comprise a memory for the storage of user commands and/or temperature schedules which define the temperature, temperatures and/or or temperature transitions of the heat exchange fluid in the peripheral circuits 312,312' which the system 300 will strive to maintain.

That is to say the flow of fluid through the circuits is controllable to provide a heat exchange rate schedule through the peripheral heat exchangers 310,310' as required, desired, pre-set, chosen and/or adjusted by the user.

At least one of the first peripheral fluid circuit pumps 318,318' and/or evaporator circuit pumps 322,322' are controllable by the controller such that the flow rates through their respective fluid circuits may be substantially equal to one another and may also be different to one another.

The system 300 may be configured to maintain the temperature of the evaporator heat exchanger fluid at a temperature different to the peripheral heat exchanger fluid. The system may additionally or alternatively be configured to maintain the temperature of the evaporator heat exchanger fluid at a temperature lower than the peripheral heat exchanger fluid.

The user may choose a temperature or schedule of temperatures for the heat exchange fluid in the first fluid circuit (i.e. in the cap 310, 310') to achieve, which translates to a heat exchange rate schedule. That is to say the flow of fluid through the circuits is controllable to provide a heat exchange rate schedule or a temperature schedule through the first heat exchanger 310,310' as required, desired, pre-set, chosen and/or adjusted by the user.

The temperature of the coolant the tank 326 is maintained, via a thermostat (not shown) and the controller 350, to a temperature which is several degrees Kelvin below that required for the heat exchanger 310,310' by the evaporator circuit 336. This differential ensures that the temperature required at the heat exchanger 310,310' is always maintained regardless of the shock load which may be applied to heat exchanger 310,310'. The actual differential will be determined by the circumstances and requirements of the heat exchanger 310,310'.

The coolant in the primary evaporator tank 326 is pumped around the heat exchanger 316,316' via pumps 322,322' which are speed controlled by the controller 350, and therefore control the flow rate of the heat exchanger fluid, which may be a coolant. The flow rate of the coolant through these circuits determines the effectiveness of the heat exchanger 316,316' in cooling the coolant in the peripheral reservoir 324, 324', which in turn partly determines the cooling effect of the heat exchanger 310,310'.

Coolant is drawn from the peripheral reservoir 324,324' via pumps 318,318' which are speed controlled by the controller 350 and control the flow rate of the coolant through the heat exchanger 310,310' and the heat exchanger 316,316'.

It is recognised that the cooling effect of the heat exchanger 310,310' is a combination of both heat exchanger fluid temperature and fluid flow rate through the heat exchanger 316,316'. For example, maximum flow rate combined with minimum temperature will provide a maximum heat exchange capability.

To illustrate this effect, consider a scenario in which pumps 322,322' are at maximum flow rate and pumps 318,318' are at minimal flow rate. The maximum heat transfer in circuit 320 is achieved. Thus the coolant temperature in the cap 310,310' is close to the coolant temperature in the primary evaporator tank 326. However maximum heat exchange in the heat exchanger 310,310' would not achieved as the flow rate of the coolant through the heat exchanger 310'310' is minimal.

As mentioned, in one example the coolant in the primary evaporator tanks 326 is maintained several degrees below the required temperature in the heat exchanger 310,310'. This enables control of the coolant temperature to be maintained at the level required in the heat exchanger 310,310' whilst also maintaining maximum flow rate to improve the cooling effect in the heat exchanger 310,310'.

The configuration of the present disclosure enables maximum or optimum coolant flow rate through the heat exchanger 310,310' at the required temperature when required to achieve maximum or optimum heat exchange in the heat exchanger 310,310'.

In one example, the coolant in the primary evaporator tank 326 may be maintained at −8 C. The pump 322,322' may be maintained at 30% full speed. This would be enough to cool the coolant in pump a circuit to −4 C with maximum flow rate.

Thus whole range of cooling parameters in the heat exchanger 310,310' can be achieved by varying the relative speeds of the pumps 322,322';318,318' and compressor 332. The effectiveness of heat exchanger 310,310' can be controlled accurately and can also be instantly changed or adjusted by adjusting flow rates rather than by waiting for heat exchanger fluids (e.g. coolants) to heat up or cool down. Additionally, the temperature regulation of each individual heat exchanger 310,310' can be accurately controlled independently of the other.

The method of control of the temperature of the coolant in the peripheral fluid circuit 312,312' can either be achieved by controlling the speed of pump 322,322' directly with a thermostat in the secondary tank 324 or indirectly controlled by measuring the heat extracted from the heat exchanger 310,310', which in turn correlates to the temperature of the object to be cooled (for example, a scalp) and adjusting the pumps 318,322;318',322' speed and coolant temperature accordingly.

That is to say, at least one each of the peripheral pumps 318, 318' and/or evaporator pumps 322,322' may be controllable in dependence upon the temperature of their respective peripheral heat exchanger fluids to regulate the fluid flow rate through their respective fluid circuits. The first peripheral pump 318 and/or evaporator pump 322 may be controllable in dependence upon a measured, determined and/or derived heat exchange rate of the first peripheral heat exchanger 310 to regulate the fluid flow rate through their respective fluid circuits.

The heat extracted from the heat exchanger 310,310' may be determined based on the difference in temperature recorded in the delivery and outlet/return tubes by the temperature sensors 340,342;340',342' respectively and the mass flow rate of fluid through the peripheral fluid circuit 312,312' measured by the flow sensor 344,344'.

Thus the fluid in the tank 326 may be maintained slightly below the chosen user temperature (as entered via the user interface 358); and the temperature of the fluid in the tank 326 may be measured by a sensor in the tank 326, which is used as a feedback to the controller 350 to control the compressor 322 to operate to thus raise/lower the fluid in tank 326 to the desired temperature.

Additionally, the fluid in the tank 324,324' (and hence fluid in peripheral circuits 312,312') is controlled in dependence upon a chosen user temperature (as entered via the user interface 358); and the temperature of the fluid in the tank 324,324' may be inferred (i.e. determined) from measurements by sensors 340,342;340',342' and/or by a temperature sensor in the tank 324,324', either or both of which may be used as a feedback to the controller 350 to operate the pumps 318,322; 318',322' to operate to thus raise/lower the fluid to the desired temperature.

There is thus provided a temperature control system which provides a significant advantage over that of the related art in that the temperature regulation flowing through a object interface heat exchanger my be more accurately and responsively controlled than with devices of the related art, regardless of how may object interface heat exchangers 310,310' are fluidly attached to the system.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A temperature control system comprising:
   a first peripheral fluid circuit for the passage of a first heat exchanger fluid, the first peripheral fluid circuit comprising:
     a first fluid connection for fluidly connecting a first peripheral heat exchanger in series with a first peripheral-evaporator heat exchanger; and
     a first peripheral pump for pumping the first heat exchanger fluid around the first peripheral fluid circuit;

a first evaporator circuit for the passage of an evaporator heat exchanger fluid through the first peripheral-evaporator heat exchanger, the first evaporator circuit comprising:
  a first evaporator pump for pumping the evaporator heat exchanger fluid around the first evaporator circuit;
  an evaporator tank in series with the first peripheral-evaporator heat exchanger and the first evaporator pump;
  the first evaporator pump being operable to pump the evaporator heat exchanger fluid from the evaporator tank to the first peripheral-evaporator heat exchanger and back to the evaporator tank;
the first evaporator circuit being fluidly isolated from the first peripheral fluid circuit;
the first peripheral-evaporator heat exchanger being configured to permit heat exchange between the first heat exchanger fluid and the evaporator heat exchanger fluid;
at least one temperature sensor in the first peripheral fluid circuit for the measurement of temperature of heat exchanger fluid in said first peripheral fluid circuit;
a controller in communication with the first peripheral pump and the first evaporator pump and which controls the pumps in dependence upon signals indicative of temperature received from the at least one temperature sensor;
a second peripheral fluid circuit for the passage of a second heat exchanger fluid, the second peripheral circuit comprising:
  a second fluid connection for fluidly connecting a second peripheral heat exchanger in series with a second peripheral-evaporator heat exchanger; and
  a second peripheral pump for pumping the second heat exchanger fluid around the second peripheral fluid circuit;
a second evaporator circuit for the passage of the evaporator heat exchanger fluid through the second peripheral-evaporator heat exchanger, the second evaporator circuit comprising:
  a second evaporator pump for pumping the evaporator heat exchanger fluid around the second evaporator circuit;
the second evaporator circuit being fluidly isolated from the second peripheral circuit and the second peripheral-evaporator heat exchanger being configured to permit heat exchange between the second heat exchanger fluid and the evaporator heat exchanger fluid; and
wherein the second peripheral heat exchanger is fluidly connected to the second fluid connection such that the second peripheral heat exchanger is in series with the second peripheral-evaporator heat exchanger and the second peripheral pump;
wherein the second evaporator circuit is in fluid communication with the evaporator tank such that the second peripheral-evaporator heat exchanger is in series with the evaporator tank and the second evaporator pump;
the second evaporator pump being operable to pump the evaporator heat exchanger fluid from the evaporator tank to the second peripheral-evaporator heat exchanger and back to the evaporator tank;
wherein the evaporator tank is provided with an evaporator that is in series fluid communication with a compressor and a condenser via a refrigerant fluid circuit to thereby provide a flow path for a refrigerant.

2. The temperature control system as claimed in claim 1, wherein a first heat exchanger fluid reservoir is provided in the first peripheral fluid circuit in series with the first peripheral-evaporator heat exchanger and the first peripheral pump.

3. The temperature control system as claimed in claim 1, wherein the first peripheral heat exchanger is fluidly connected to the first fluid connection such that the first peripheral heat exchanger is in series with the first peripheral-evaporator heat exchanger and first peripheral pump.

4. The temperature control system as claimed in claim 1, wherein a second heat exchanger fluid reservoir is provided in the second peripheral circuit in series with the second peripheral-evaporator heat exchanger and second peripheral pump.

5. The temperature control system as claimed in claim 1, wherein each of the first peripheral fluid circuit and the second peripheral fluid circuit are closed.

6. The temperature control system as claimed in claim 1, wherein the first peripheral fluid circuit is fluidly isolated from the second peripheral fluid circuit.

7. The temperature control system as claimed in claim 1, wherein one of the temperature sensors is upstream of the first peripheral heat exchanger, and a second one of the temperature sensors is downstream of the first peripheral heat exchanger.

8. The temperature control system as claimed in claim 1, wherein the first peripheral pump, the second peripheral pump, and the first and second evaporator pumps are controllable in dependence upon the temperature of their respective peripheral heat exchanger fluids to regulate the fluid flow rate through their respective fluid circuits.

9. The temperature control system as claimed in claim 1, wherein at least one of the first peripheral pump and the first evaporator pump are controllable in dependence upon a measured, determined and derived heat exchange rate of the first peripheral heat exchanger to regulate the fluid flow rate through their respective fluid circuits.

10. The temperature control system as claimed in claim 1, wherein at least one of the first and second peripheral pumps and the first and second evaporator pumps are controllable such that flow rates through their respective fluid circuits may be substantially equal to one another and may also be different to one another.

11. The temperature control system as claimed in claim 1, wherein the system is configured to maintain a temperature of the evaporator heat exchanger fluid at a temperature different to the first heat exchanger fluid.

12. The temperature control system as claimed in claim 1, wherein the system is configured to maintain the temperature of the evaporator heat exchanger fluid at a temperature lower than the first heat exchanger fluid.

13. The temperature control system as claimed in claim 1, wherein the flow of the evaporator heat exchanger fluid, the first heat exchanger fluid, and the second heat exchanger fluid through the circuits is controllable to provide a heat exchange rate schedule through the first and second peripheral heat exchangers is adjustable by the user.

14. The temperature control system as claimed in claim 1, wherein the evaporator tank comprises a fluid reservoir and the first and second evaporator circuits extend through the evaporator tank and are submerged within the reservoir.

15. The temperature control system as claimed in claim 14, wherein the first evaporator circuit enters into the evaporator tank from a first side and the second evaporator circuit enters into the evaporator tank from an opposing second side.

16. The temperature control system as claimed in claim 14, wherein the evaporator is submerged within the fluid reservoir.

17. The temperature control system as claimed in claim 14, wherein the evaporator tank is positioned between the first and second peripheral-evaporator heat exchangers.

* * * * *